US012279827B2

(12) United States Patent
Kang et al.

(10) Patent No.: US 12,279,827 B2
(45) Date of Patent: Apr. 22, 2025

(54) SYSTEM AND METHOD FOR SURGICAL PLANNING

(71) Applicant: MAKO Surgical Corp., Weston, FL (US)

(72) Inventors: Hyosig Kang, Weston, FL (US); Daniel Odermatt, Fort Lauderdale, FL (US); Alon Mozes, Miami Beach, FL (US); Chunyan Wu, Parkland, FL (US); Miranda Jamieson, Fort Lauderdale, FL (US)

(73) Assignee: MAKO Surgical Corp., Weston, FL (US)

( * ) Notice: Subject to any disclaimer, the term of this patent is extended or adjusted under 35 U.S.C. 154(b) by 425 days.

(21) Appl. No.: 17/695,303

(22) Filed: Mar. 15, 2022

(65) Prior Publication Data
US 2022/0202498 A1  Jun. 30, 2022

Related U.S. Application Data

(63) Continuation of application No. 16/705,423, filed on Dec. 6, 2019, now Pat. No. 11,304,758, which is a continuation of application No. 15/667,306, filed on Aug. 2, 2017, now Pat. No. 10,531,924, which is a continuation of application No. 13/178,148, filed on Jul. 7, 2011, now abandoned.

(60) Provisional application No. 61/442,503, filed on Feb. 14, 2011, provisional application No. 61/503,606, filed on Jun. 30, 2011.

(51) Int. Cl.
*A61B 34/10* (2016.01)

(52) U.S. Cl.
CPC ........ *A61B 34/10* (2016.02); *A61B 2034/107* (2016.02); *G06V 2201/033* (2022.01)

(58) Field of Classification Search
CPC ..... A61B 34/10; A61B 17/16; A61B 17/1666; A61B 17/1631; A61B 17/162
See application file for complete search history.

(56) References Cited

U.S. PATENT DOCUMENTS

| 7,594,933 | B2 | 9/2009 | Kammerzell et al. |
| 7,634,306 | B2 | 12/2009 | Sarin et al. |
| 7,877,131 | B2 | 1/2011 | Jansen et al. |
| 10,531,924 | B2 * | 1/2020 | Kang ..................... A61B 34/10 |
| 2004/0087852 | A1 * | 5/2004 | Chen ..................... A61B 6/547 |
| | | | 600/407 |
| 2005/0148855 | A1 | 7/2005 | Kienzle, III |
| 2006/0264731 | A1 | 11/2006 | Murphy |

(Continued)

OTHER PUBLICATIONS

D.W. Murray, The Definition And Measure Of Acetabular Definition, The Journal of Bone & Joint Surgery, Mar. 1993, pp. 228-232, vol. 85-B, No. 2.

(Continued)

*Primary Examiner* — Christopher J Beccia

(74) *Attorney, Agent, or Firm* — FOLEY & LARDNER LLP

(57) ABSTRACT

A method includes obtaining a model of a bone of a patient, identifying a plurality of landmarks of the model of the bone, defining a plane of the patient, determining an axis based on the plurality of landmarks and the plane, and planning a planned pose of an implant relative to the bone based on a relationship between a model of the implant, the axis, and the plane.

20 Claims, 6 Drawing Sheets

(56) References Cited

U.S. PATENT DOCUMENTS

| | | |
|---|---|---|
| 2010/0030231 A1 | 2/2010 | Revie et al. |
| 2010/0249796 A1 | 9/2010 | Nycz |
| 2011/0082468 A1 | 4/2011 | Hagag et al. |
| 2011/0152871 A1* | 6/2011 | Park ............... A61B 34/30 |
| | | 901/14 |

OTHER PUBLICATIONS

Jurgen W. Babisch, Frank Layher and Louis-Philippe Amiot, The Rationale for Tilt-Adjusted Acetabular Cup Navigation, The Journal of Bone & Joint Surgery, pp. 357-365, Feb. 2008, vol. 90-A-No. 2, The Journal of Bone & Joint Surgery—Needham, MA United States of America.

Zhinian Wan MD, Aamer Malik MD, Branislav Jaramaz PhD, Lisa Chao BS, Lawrence D. Dorr MD, Imaging and Navigation Measurement of Acetabular Component Position in THA, Symposium: Papers Presented at the HIP Society Meetings 2008, Jan. 2009, pp. 32-42, vol. 467, No. 1.

\* cited by examiner

SYSTEM AND METHOD FOR SURGICAL PLANNING

CROSS-REFERENCE TO RELATED PATENT APPLICATIONS

This application is a continuation of U.S. patent application Ser. No. 16/705,423, filed Dec. 6, 2019, which is a continuation of U.S. patent application Ser. No. 15/667,306, filed Aug. 2, 2017, which is a continuation of U.S. patent application Ser. No. 13/178,148, filed Jul. 7, 2011, which claims the benefit of and priority to U.S. Provisional Patent Application No. 61/503,606, filed on Jun. 30, 2011, and U.S. Provisional Patent Application No. 61/442,503, filed on Feb. 14, 2011. All of these applications are incorporated by reference herein in their entireties.

TECHNICAL FIELD

The present disclosure relates generally to computer-assisted surgical procedures, and more particularly, to systems and methods for planning an orientation of a prosthetic device.

BACKGROUND

Computer-assisted surgery (CAS) systems may be used for various surgical applications including hip replacement surgery. For instance, a CAS system may be used in determining the appropriate version and inclination angle of a prosthetic acetabular cup to be implanted into a patient during a surgical procedure on a hip joint. Version and inclination of an acetabular cup can be calculated relative to various anatomic planes and axes. Evidence suggests that it may be advantageous to calculate version and inclination relative to a coronal radiographic plane. Existing CAS methods for calculating version and inclination relative to a coronal radiographic plane often involve intraopertative identification of landmarks on the pelvis which increase patient post-surgical discomfort and/or increase the time required to perform the surgical procedure Accordingly, there is a need for a simplified system and method to plan and perform a surgical procedure to implant an acetabular cup according to a defined version and inclination relative to a coronal radiographic plane. Moreover, there is a need to enable more accurate calculations of version and inclination with minimal intraoperative manipulations to the patient. Furthermore, there is a need to reduce the overall time that is spent on anesthetizing and performing surgical procedures on the patient.

SUMMARY OF THE DISCLOSURE

In one aspect of the present disclosure, a method of planning and performing a surgical procedure is provided. The method may determine a coronal radiographic plane of a patient based on a medical image of the patient's pelvis, identify two landmarks within the medical image, and determine a version and inclination of a virtual model of an acetabular cup based on a relationship between the virtual model of the acetabular cup, the coronal radiographic plane, and the two landmarks.

In another aspect of the disclosure, a method of planning and performing a surgical procedure is provided. The method may receive a medical image of a patient's pelvis, determine a coronal radiographic plane of the patient based on the medical image, identify two landmarks within the medical image, determine a longitudinal axis based on the two landmarks and the coronal radiographic plane, and determine a version and an inclination of a virtual model of an acetabular cup based on a relationship between the virtual model of the acetabular cup, the coronal radiographic plane, and the longitudinal axis.

In yet another aspect of the disclosure, a system for planning and performing a surgical procedure is provided. The system may include an input device, an output device, and a controller in communication with each of the input device and output device. The controller may be configured to access a medical image of a patient's pelvis, determine a coronal radiographic plane of the patient based on the medical image, identify two landmarks within the medical image, and determine a version and inclination of a virtual model of an acetabular cup based on a relationship between the virtual model of the acetabular cup, the coronal radiographic plane, and the two landmarks.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make certain references to orthopedic procedures involving hip joints, it should be understood that the subject matter described herein may be applicable to other joints in the body, such as, for example, shoulders, elbows, wrists, spines, knees, ankles, and the like.

Figure 2:
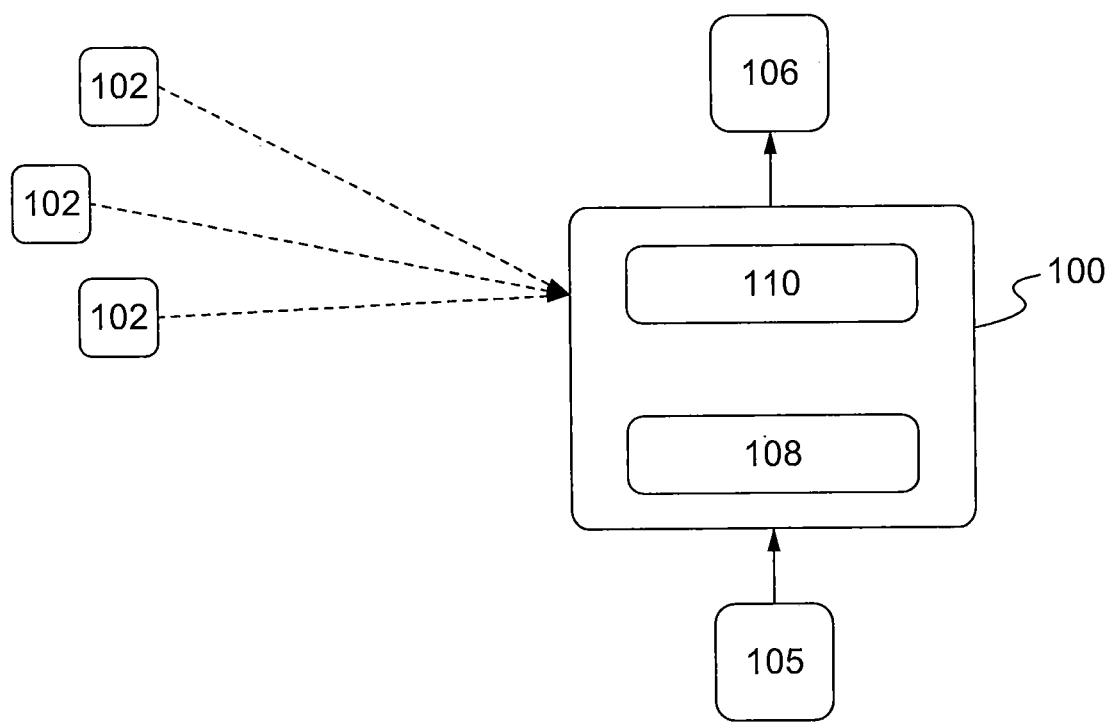
FIG. 2 is a schematic view of an exemplary computer-assisted system for determining pelvic tilt.

Referring to FIG. 2, one exemplary embodiment of a computer-assisted surgical (CAS) system 100 which may be used to plan a surgical procedure is provided. As shown, the CAS system 100 may be in direct or indirect communication with one or more medical imaging devices 102 and configured to receive one or more medical images of a patient's anatomy that have been captured by the medical imaging devices 102. More specifically, the CAS system 100 may be configured to receive medical images from a medical imaging device 102 over wired and/or wireless connections, over a network, such as a local area network (LAN), a wide area network (WAN), and the like. The CAS system 100 may also be configured to retrieve medical images that have been captured by a medical imaging device 102 and stored within a database that is either locally or remotely stationed relative to the CAS system 100. The medical imaging devices 102 may include any one or more of a computed tomography (CT) device, a magnetic resonance imaging (MRI) device, an X-ray device, a fluoroscopic imaging device, an ultrasound device, any other device commonly used for medical imaging. The medical image may include a three-dimensional image output from a medical imaging device 102 or a three-dimensional model based on an image or series of images output from a medical imaging device 102.

Still referring to FIG. 2, the CAS system 100 may generally include an input device 105, an output device 106, a memory 108 and a controller 110. The input device 105 may include any one or more of a keyboard, a mouse, a trackball, a touch screen, a touch pad, a microphone, a dial, a switch, a button, a camera, and any other device suited to receive information from a user, such as a surgeon, or the like. The output device 106 may include any one or more of a liquid crystal display (LCD), a cathode ray tube (CRT) display, a plasma screen, a touch screen, and any other device suited to output information to the user. For example, using the input device 105, the user may be able to manipulate orientations and/or views of medical images as well as input parameters that may be required by the CAS system 100. Additionally, using the output device 106, the user may be able to access or view the results of the manipulations as well as any calculations that are performed by the CAS system 100. Furthermore, the memory 108 of the CAS system 100 may be used to locally and at least temporarily store one or more medical images as well as any other data that may be relevant to a particular patient and required by the controller 110. The memory 108 may also be configured to store one or more algorithms or software by which the controller 110 may be operated. In turn, the controller 110 may be configured to electrically communicate with each of the input device 105, output device 106 and the memory 108 and execute tasks according to the algorithms provided.

Figure 3:
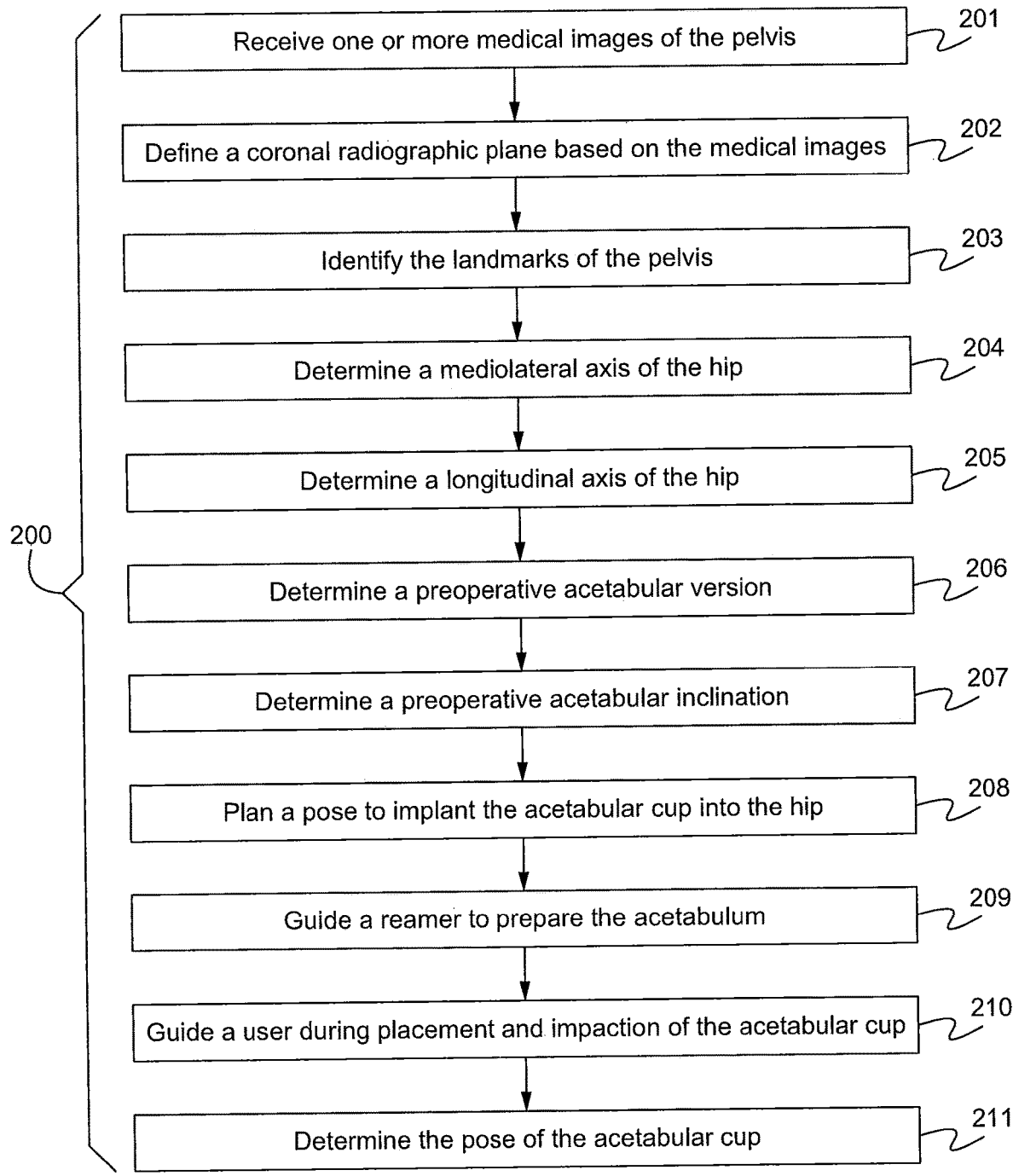
FIG. 3 is a diagrammatic view of an exemplary method for determining pelvic tilt.

Turning to FIG. 3, one exemplary algorithm or method 200 by which the controller 110 may operate to plan the version and inclination of a prosthetic acetabular cup 22 is provided. Initially, in step 201, the controller 110 of the CAS system 100 may be configured to receive one or more medical images provided by, for instance, a medical imaging device 102. More specifically, the controller 110 may be configured to access or receive, for instance, a medical image of a patient's pelvis 10, captured while the patient is in the supine position.

Figure 4:
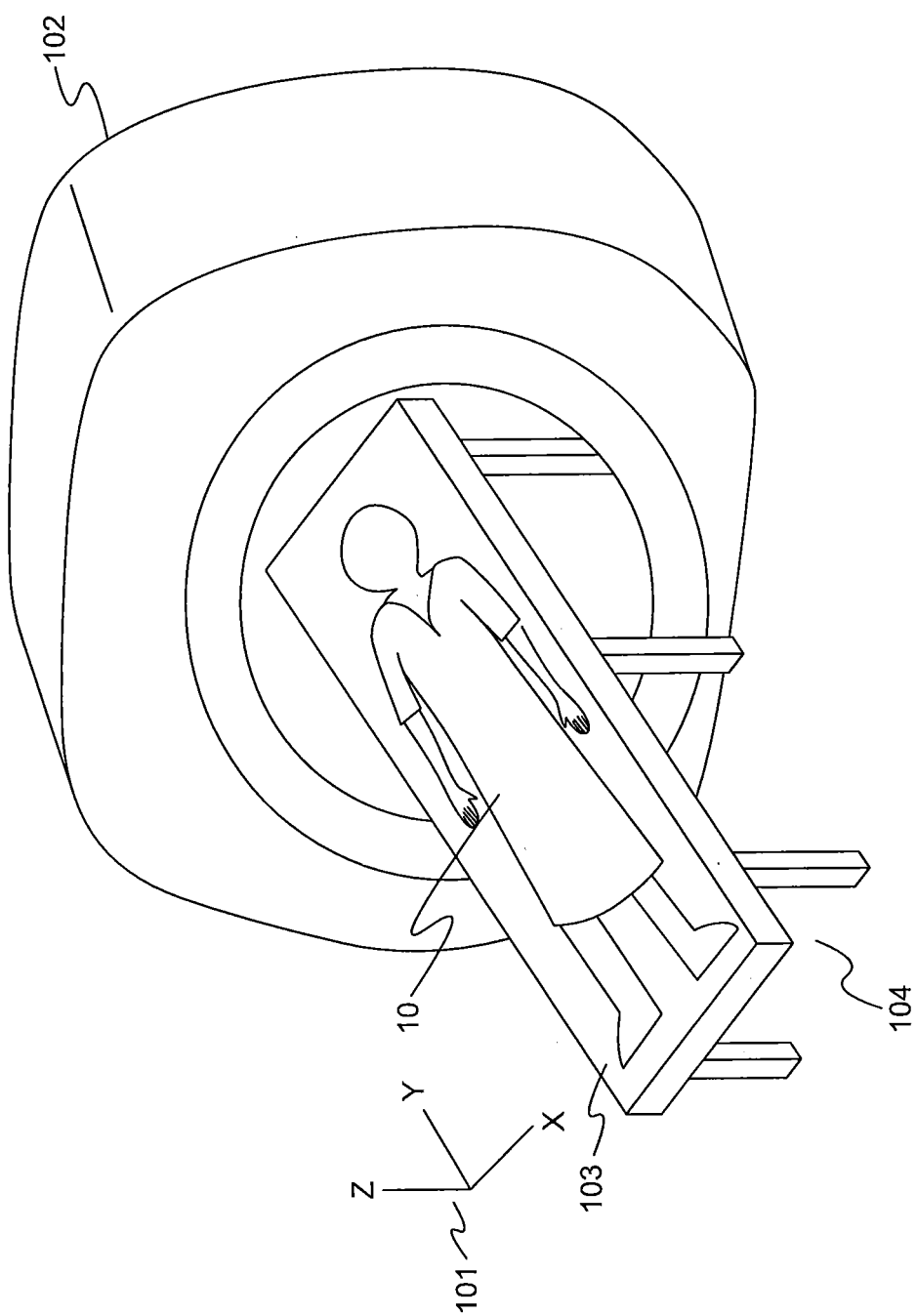
FIG. 4 is a graphical view of an exemplary medical imaging device.

In step 202, the controller 110 may be configured to define a coronal radiographic plane 18 based on a plane associated with the medical image. As illustrated in FIG. 4, the medical imaging device 102 may be associated with a device coordinate system 101, and the medical image produced by the medical imaging device 102 may include information relating the image of the anatomy to the device coordinate system 101. In certain embodiments, the device coordinate system 101 may relate directly to the coordinate system of the medical image. In the embodiment illustrated in FIG. 4, the x-y plane of the device coordinate system 101 is substantially parallel to a surface plane 103, which is defined by the surface of a table 104, or other patient supporting structure, on which a patient lies in a supine position while the medical imaging device 102 captures the medical image of a portion of the patient's anatomy. More particularly, the x-axis may run substantially along the width of the table 104 and may be similar in orientation to a mediolateral axis 16 of the patient, and the y-axis may run substantially along the length of the table 104 and may be similar in orientation to a longitudinal axis 17 of the patient. Thus, according to the embodiment illustrated in FIG. 4, the controller 110 may be able to identify the surface plane 103 as the x-y plane of the medical image, which relates directly to the x-y plane of the device coordinate system 101. In another embodiment, known information regarding the physical structure of the medical imaging device 102, as it relates to the structure and content of the data in the medical image, may be used to transform a plane represented in the medical image that is not substantially parallel to the surface of the table 104 into a plane that is substantially parallel to the surface of the table 104. In yet another embodiment, the medical images provided to the controller 110 may include information from which the controller 110 can determine the surface plane 103 or other plane substantially parallel with the surface of the table 104, or other patient supporting structure, on which a patient lies in a supine position while the medical imaging device 102 captures the medical image of a portion of the patient's anatomy. Such information could include, for example, image data that is captured in the medical image and is representative of the surface of the table 104. In yet another embodiment, the controller 110 may be configured to manually receive information pertaining to the surface plane 103 from a user through the input device 105, such as, for example, a user manually selecting multiple points representing the surface of the table 104 in the medical image. The controller 110 may then designate the surface plane 103, or a plane parallel thereto, as the coronal radiographic plane 18. Thus, in at least one embodiment, the coronal radiographic plane 18 is defined as the x-y plane of the device coordinate system 101.

Figure 1:
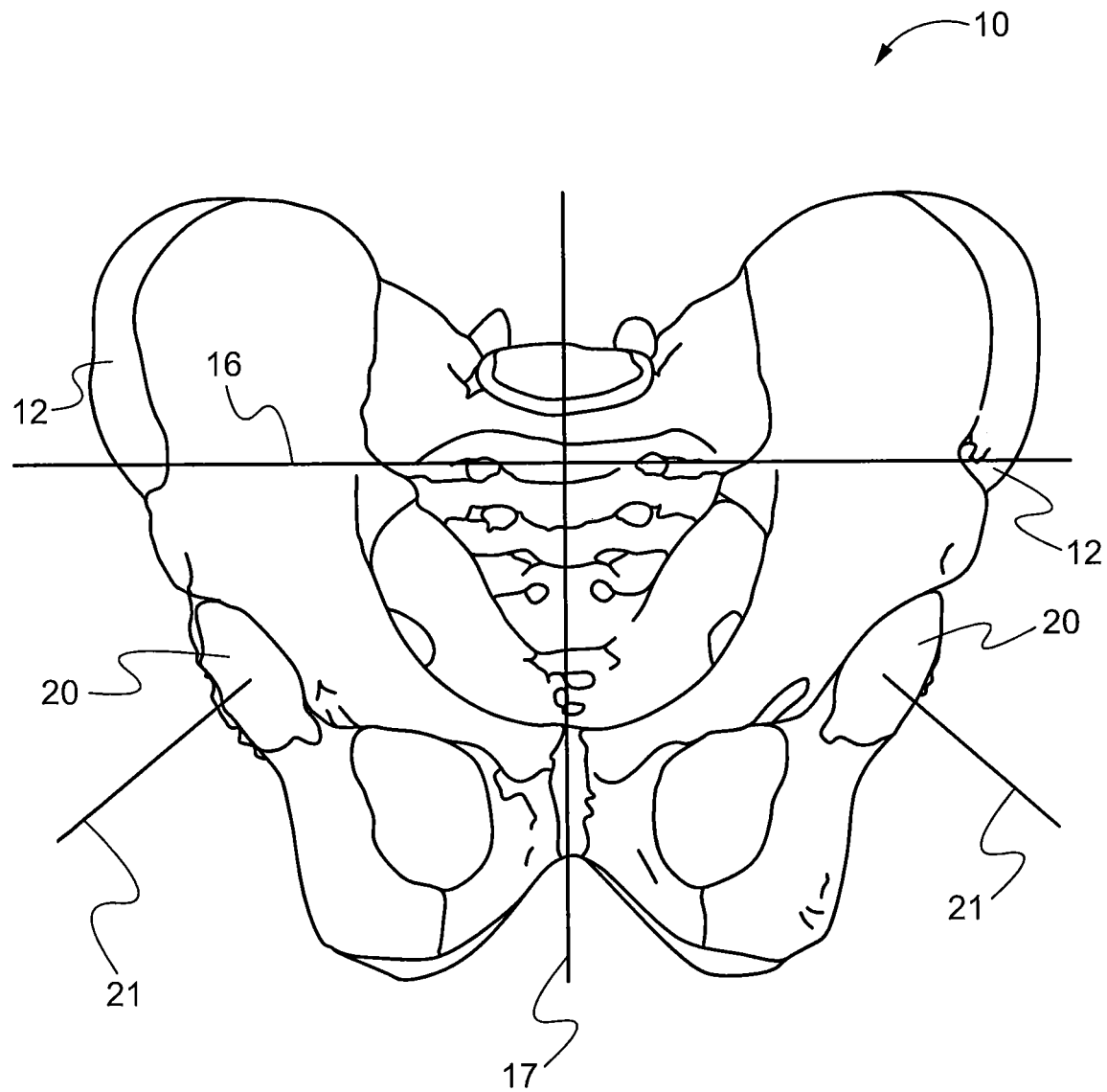
FIG. 1 is a graphical view of a pelvis.

In step 203, the controller 110 may be configured to identify a plurality of landmarks within the medical image of the pelvis 10. For instance, the controller 110 may be configured to identify two anterior-superior iliac spines 12 of the pelvis 10, as shown in FIG. 1. The controller 110 may be configured to receive information pertaining to the respective locations of the anterior-superior iliac spines 12 from a user. For example, a user viewing the medical images of the pelvis 10 at the output device 106 may visually locate and manually input the locations of one or both of the anterior-superior iliac spines 12 into the controller 110 via the input device 105. In another embodiment, the controller 110 may be configured to automatically detect and extract information pertaining to the locations of the anterior-superior iliac spines 12 of the pelvis 10 using image detection and/or other related schemes on the medical images. While the embodiments described herein discuss the use of the two iliac spines 12 of the pelvis 10, various pairs of landmarks within the patient's anatomy that are generally known to be substantially symmetrical about a median plane of the patient's anatomy may be alternatively used, such as the two ischial spines of the pelvis 10.

In step 204 of the algorithm 200 of FIG. 3, the controller 110 may be configured to determine a mediolateral axis 16 of the pelvis 10 based on the positions within the medical image of the landmarks determined in step 203. More specifically, the controller 110 may generate a line that intersects each of the landmarks, such as the two anterior-superior iliac spines 12, and designate the resulting line as the mediolateral axis 16, as illustrated in FIG. 1. In one embodiment, the mediolateral axis 16 may be manually identified to the controller 110 by the user. For example, while viewing the medical images of the pelvis at the output device 106, the user may manually identify the line that intersects each of the anterior-superior iliac spines 12 using the input device 105. Once identified, the controller 110 may designate the line as the mediolateral axis 16. In an alternative embodiment, the controller 110 may be configured to automatically detect the mediolateral axis 16 by calculating the line of intersection between each of the identified landmarks of the pelvis 10. In still further alternatives, the controller 110 may be configured to determine at least one vector based on the anterior-superior iliac spines 12 determined in step 203. For instance, once the anterior-superior iliac spines 12 of the pelvis 10 have been identified, the controller 110 may form a three-dimensional vector extending between or intersecting both of the anterior-superior iliac spines 12 to form the mediolateral axis 16.

Once the mediolateral axis 16 has been determined, the controller 110 in step 205 may be configured to determine a longitudinal axis 17 relative to the medical image of the pelvis 10, as illustrated in FIG. 1. The controller 110 may determine the longitudinal axis 17 as a line that is substantially transverse to the mediolateral axis 16 and substantially parallel with, or contained in, the coronal radiographic plane 18. The longitudinal axis 17 may also be constrained to intersect with the mediolateral axis 16 at a midpoint between the two landmarks, for example the two iliac spines 12. In another embodiment, step 205 may include applying a correction to the radiographic coronal plane 18 based on the determined mediolateral axis 16. In particular, with reference to the embodiment in which the coronal radiographic plane is defined as the x-y plane of the device coordinate system 101, as discussed in association with FIG. 4, a unit vector having the orientation of the x-axis in the device coordinate system 101 may be crossed with a unit vector having the same orientation as the mediolateral axis 16 to produce a rotation vector. In this embodiment, the radiographic coronal plane 18 may be rotated about the rotation vector until the x-axis of the coronal radiographic plane is parallel to, or collinear with, the mediolateral axis 16.

Figure 5:
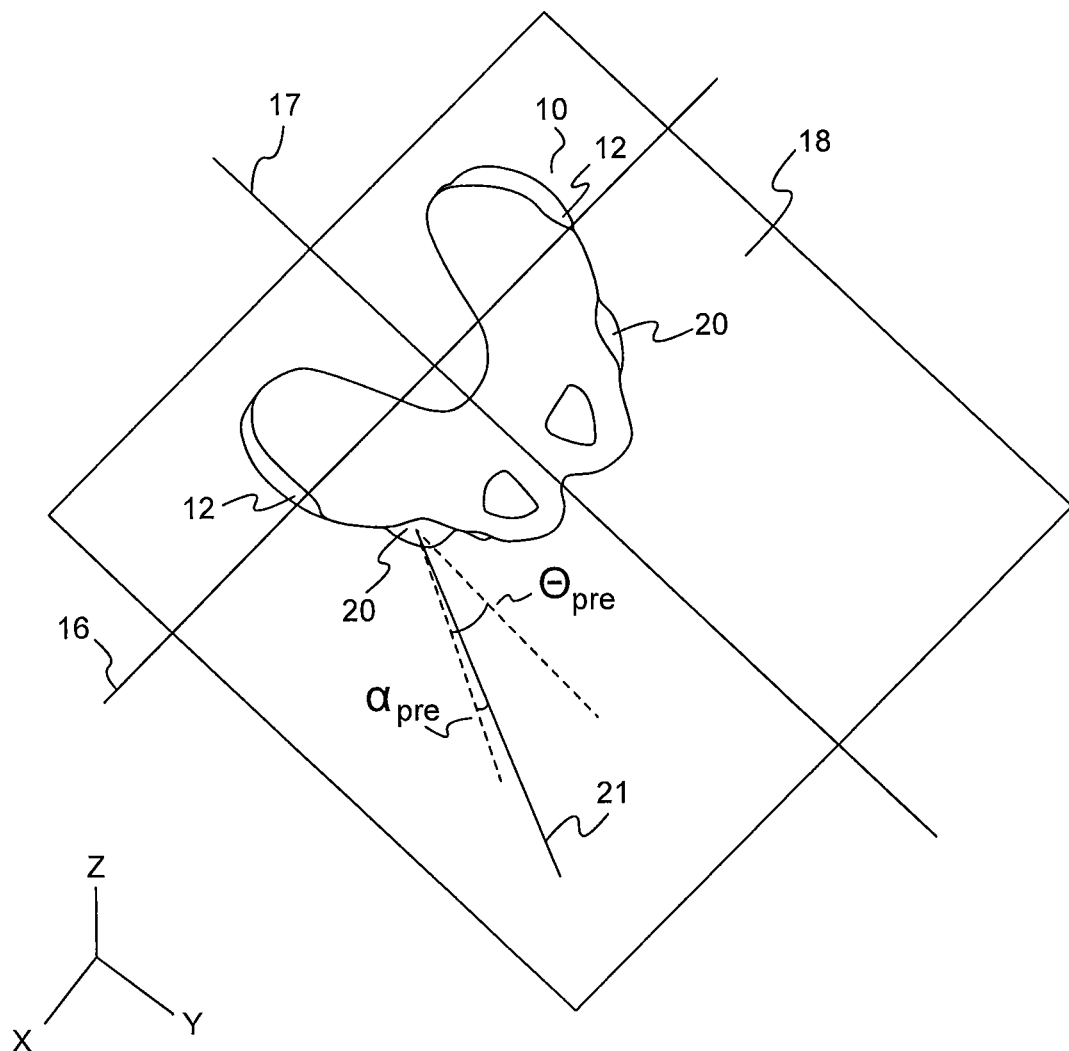
FIG. 5 is a diagrammatic view of a preoperative orientation of an acetabulum.

In step 206, the controller 110 may be configured to determine a preoperative acetabular version ($\alpha_{pre}$). The controller 110 may determine a patient's acetabular axis 21 based on the patient's acetabulum 20, as illustrated in FIG. 1, according to various methods that are known in the art. The patient's preoperative version ($\alpha_{pre}$) may then be determined as the angle between the acetabular axis 21 and the coronal radiographic plane 18, as illustrated in FIG. 5.

In step 207 the controller 110 may be configured to determine a preoperative acetabular inclination ($\theta_{pre}$). The preoperative acetabular inclination ($\theta_{pre}$) may be determined as the angle between the longitudinal axis 17 and the projection of acetabular axis 21 onto the coronal radiographic plane 18, as illustrated in FIG. 5.

Figure 6:
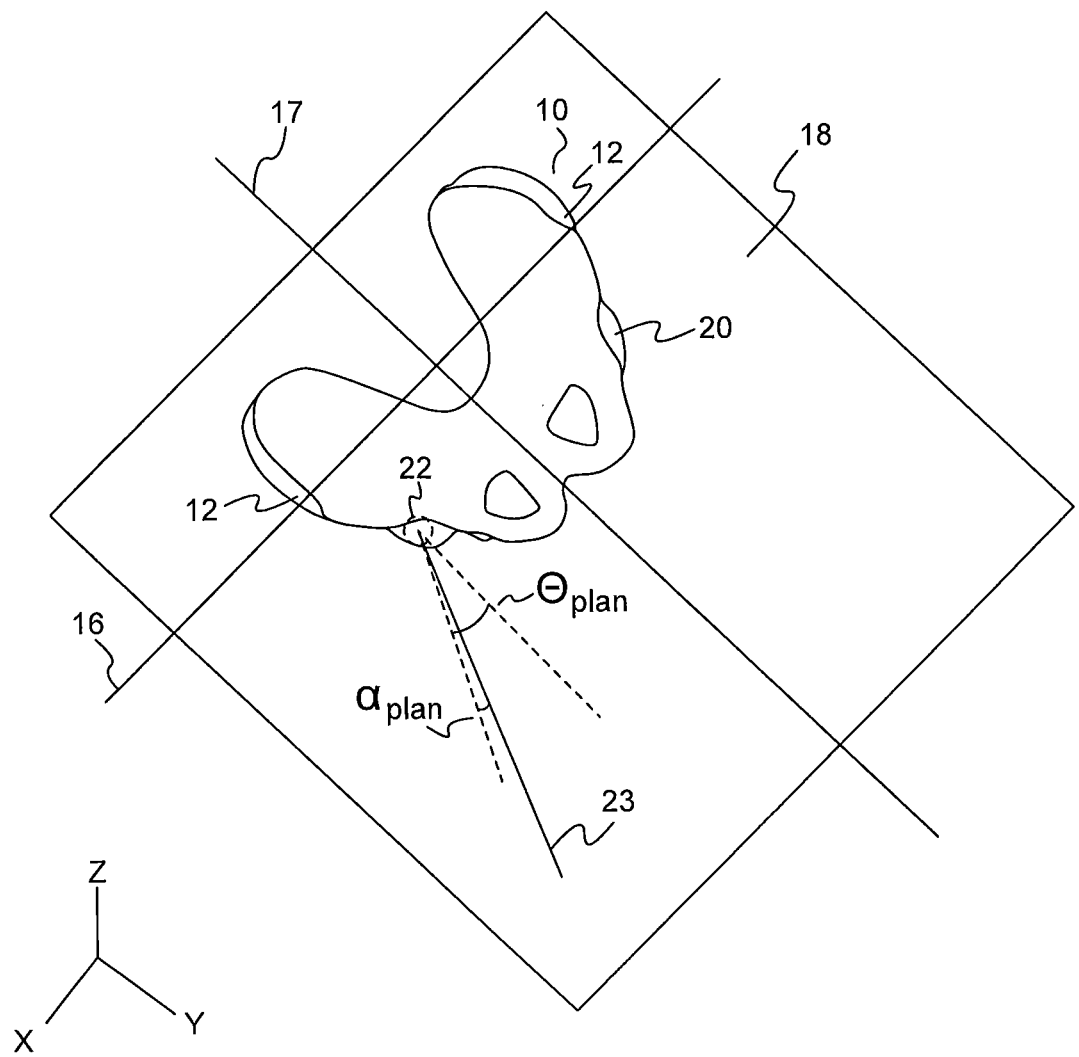
FIG. 6 is a diagrammatic view of a planned pose of an acetabular cup.

With reference to FIG. 6, in step 208 the controller 110 may be configured to plan a pose to implant the acetabular cup 22 into a patient's pelvis 10. As used herein, "pose" means position and orientation. The acetabular cup 22 may have an acetabular cup axis 23 associated with it. The acetabular cup axis 23 may be pass through the center of the acetabular cup 23, and may be substantially normal to the center of the acetabular cup 23 and/or the rim of the acetabular cup 23. The acetabular cup axis 23 may also be determined based on other methods that may be known in the art. In this step a user may position a virtual model of the acetabular cup 22 relative to the medical image of the patient's pelvis 10 by way of the input device 105. Based on the orientation of the virtual model of the acetabular cup 22, the controller 110 may then determine a planned version ($\alpha_{plan}$) and inclination ($\theta_{plan}$) for the acetabular cup 22, and the planned version ($\alpha_{plan}$) and inclination ($\theta_{plan}$) may be provided to a user by way of the output device 106. As illustrated in FIG. 6, the planned version ($\alpha_{plan}$) may be determined as the angle between acetabular cup axis 23 and coronal radiographic plan 18. The planned inclination ($\theta_{plan}$) may be determined as the angle between longitudinal axis 17 and the projection of the acetabular cup axis 23 onto the coronal radiographic plane 18.

Alternatively, the controller 110 may be configured to receive the planned version ($\alpha_{plan}$) and inclination ($\theta_{plan}$) and constrain the virtual model of the acetabular cup 22 accordingly. According to this alternative embodiment, a user may input a desired planned version ($\alpha_{plan}$) and inclination ($\theta_{plan}$) by way of the input device 105, and the controller 110 would use these values to constrain the orientation of the virtual model of the acetabular cup 22, while allowing the user to adjust the position of the virtual model of the acetabular cup 22 relative to medical image of the pelvis 10.

In step 209, the controller 110 may be configured to guide a reamer to prepare the acetabulum 20 such that the implanted acetabular cup 22 is substantially oriented according to the planned version ($\alpha_{plan}$) and inclination ($\theta_{plan}$) of the acetabular cup 22. This may be accomplished, for example, by providing surgical navigation and haptic feedback to a user manipulating the reamer, as described in U.S. Patent Application Publication US 2011/0082468, which is hereby incorporated by reference.

In step 210, the controller 110 may be configured to guide a user during placement and impaction of the acetabular cup 22 to substantially achieve the planned version ($\alpha_{plan}$) and inclination ($\theta_{plan}$) of the acetabular cup 22. This may be accomplished, for example, by providing surgical navigation and haptic feedback to a user manipulating an impactor tool, as further described in U.S. Patent Application Publication US 2011/0082468.

In step 211, the controller 110 may be configured to determine the pose of the acetabular cup 22 after impaction into the pelvis 10 as described in U.S. Patent Application Publication US 2011/0082468. The controller may then use the post-impaction pose of the acetabular cup 22 relative to the pelvis 10 to determine a post-impaction version ($\alpha_{post}$) and inclination ($\theta_{post}$) of the acetabular cup in a manner similar to that discussed in step 208. The post-impaction version ($\alpha_{post}$) and inclination ($\theta_{post}$) may then be displayed to a user by way of the output device 106.

While only certain embodiments have been set forth for the purposes of illustration, alternatives and modifications will be apparent from the above description to those skilled in the art. These and other alternatives are considered equivalents and within the scope of this disclosure and the appended claims.

What is claimed is:

1. A system for facilitating surgical placement of an implant at a patient's bone, the system comprising:
a non-transitory memory device storing instructions, that, when executed by a processor, cause the processor to perform tasks comprising:
obtaining a representation of the patient's bone;
identifying pairs of landmarks on the representation of the patient's bone;
generating, for each pair of landmarks, a line intersecting the landmarks;
determining, using the plurality of lines, a coordinate system for identifying a version and inclination of an implant; and
guiding, using the coordinate system, the surgical placement of the implant onto the patient's bone consistent with a plan for the version and the inclination of the implant relative to the patient's bone.

2. The system of claim 1, wherein determining the coordinate system comprises determining an anatomical plane of a body of the patient.

3. The system of claim 2, wherein the anatomical plane is a coronal plane.

4. The system of claim 1, wherein the patient's bone is a pelvis.

5. The system of claim 4, wherein the implant is an acetabular cup.

6. The system of claim 1, wherein one of the lines is a longitudinal axis of the patient.

7. The system of claim 1, wherein one of the lines is a mediolateral axis of the patient.

8. The system of claim 1, comprising an impactor tool, wherein guiding the surgical placement of the implant consistent with the plan for the version and inclination of the implant comprises causing haptic feedback to be provided to a user manipulating the impactor tool.

9. The system of claim 1, comprising a robotic device, wherein guiding the surgical placement comprises controlling the robotic device to facilitate implantation of the implant in accordance with the plan.

10. The system of claim 1, wherein identifying the pairs of landmarks comprises accepting user input selecting points on the representation of the patient's bone.

11. The system of claim 1, wherein the representation of the patient's bone is a medical image of the patient's bone.

12. A method, comprising:
obtaining a representation of a bone of a patient;
identifying pairs of landmarks on the representation of the bone;
generating lines intersecting the pairs of landmarks;
determining, using the lines, a coordinate system for identifying pose of an implant relative to the bone of the patient; and
guiding, via haptic feedback and based on the coordinate system, implantation of the implant on the bone in a planned pose.

13. The method of claim 12, wherein the coordinate system identifies an anatomical plane of a body of the patient.

14. The method of claim 12, wherein the bone is a pelvis and the implant is an acetabular cup, and wherein the planned pose comprises a version and inclination of the acetabular cup.

15. The method of claim 12, comprising determining the planned pose by determining a planned inclination and a planned version based on the relationship between a model of the implant and the coordinate system.

16. The method of claim 12, wherein guiding, via the haptic feedback, the implantation of the implant comprises providing haptic feedback to a user manipulating an impactor tool.

17. A non-transitory memory device storing instructions, which, when executed by one or more processors, cause the one or more processors to perform tasks comprising:
obtaining a model of a bone of a patient;
identifying a plurality of landmarks of the model of the bone;
defining a plane of the patient;
determining an axis based on the plurality of landmarks and the plane; and
facilitating planning of a surgical placement of an implant onto the bone by determining a planned pose of the implant relative to the bone based on a relationship between a model of the implant, the axis, and the plane.

18. The non-transitory memory device of claim 17, wherein the plane of the patient is an anatomical plane of a body of the patient.

19. The non-transitory memory device of claim 17, wherein the tasks further comprise controlling a robotic device to guide the surgical placement in accordance with the planned pose.

20. The non-transitory memory device of claim 17, wherein determining the planned pose comprises determining a planned version or a planned inclination based on the relationship between the model of the implant, the axis, and the plane.

* * * * *